United States Patent
Eckardt

(10) Patent No.: US 9,267,865 B2
(45) Date of Patent: Feb. 23, 2016

(54) METHOD AND PARTICLE SENSOR FOR DETECTING PARTICLES IN AN EXHAUST GAS STREAM

(75) Inventor: Martin Eckardt, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 452 days.

(21) Appl. No.: 13/700,567

(22) PCT Filed: Apr. 15, 2011

(86) PCT No.: PCT/EP2011/055976
§ 371 (c)(1),
(2), (4) Date: Feb. 12, 2013

(87) PCT Pub. No.: WO2011/151104
PCT Pub. Date: Dec. 8, 2011

(65) Prior Publication Data
US 2013/0247648 A1    Sep. 26, 2013

(30) Foreign Application Priority Data
Jun. 1, 2010 (DE) .......... 10 2010 029 575

(51) Int. Cl.
*G01N 7/00* (2006.01)
*G01M 15/10* (2006.01)
(Continued)

(52) U.S. Cl.
CPC ......... *G01M 15/102* (2013.01); *G01N 15/0266* (2013.01); *G01N 15/0656* (2013.01); *F01N 2560/05* (2013.01); *F02D 41/1466* (2013.01)

(58) Field of Classification Search
CPC ............ F01N 2560/05; F01N 2560/00; F02D 41/1466; G01M 15/102
USPC .................................. 73/23.31, 114.71, 304 C
See application file for complete search history.

(56) References Cited

U.S. PATENT DOCUMENTS 3,469,157 A * 9/1969 Rhodes ............... G01V 3/088
111/903
3,628,139 A * 12/1971 Huber ............... G01N 15/0656
340/632

(Continued)

FOREIGN PATENT DOCUMENTS

| CN | 86 1 03084 A | 1/1988 |
| CN | 101281154 A | 10/2008 |

(Continued)

OTHER PUBLICATIONS

International Search Report corresponding to PCT Application No. PCT/EP2011/055976, mailed Jul. 18, 2011 (German and English language document) (7 pages).

*Primary Examiner* — Truong Phan
(74) *Attorney, Agent, or Firm* — Maginot, Moore & Beck LLP

(57) ABSTRACT

A method for detecting particles, for example in an exhaust gas stream of a vehicle in which the exhaust gas stream is guided along a duct, includes using a particle sensor that has at least two electrodes arranged in the duct. The method includes applying a first voltage and a second voltage to the electrodes to produce a first electric field and a second electric field between the electrodes. The method also includes ascertaining a first capacitance value corresponding to the first electric field and a second capacitance value corresponding to the second electric field of a capacitor formed by the electrodes. Information relating to the particles contained in the exhaust gas stream is ascertained from the first capacitance value and the second capacitance value.

9 Claims, 1 Drawing Sheet

(51) Int. Cl.
*G01N 15/02* (2006.01)
*G01N 15/06* (2006.01)
*F02D 41/14* (2006.01)

(56) References Cited

U.S. PATENT DOCUMENTS

| | | | | |
|---|---|---|---|---|
| 4,580,441 | A | * | 4/1986 | Sakurai .................... F01N 3/028 250/250 |
| 4,916,384 | A | * | 4/1990 | Ishida .......................... 324/71.4 |
| 7,350,397 | B2 | * | 4/2008 | Pidria ................ G01N 15/0656 73/23.33 |
| 2007/0119233 | A1 | * | 5/2007 | Schnell ............. G01N 15/0656 73/28.01 |
| 2008/0034839 | A1 | * | 2/2008 | Ante et al. ................... 73/23.31 |
| 2008/0048681 | A1 | | 2/2008 | Birkhofer et al. |
| 2009/0188300 | A1 | | 7/2009 | Gaultieri et al. |
| 2009/0217745 | A1 | * | 9/2009 | Schneider et al. ......... 73/114.71 |
| 2009/0295400 | A1 | * | 12/2009 | Wilhelm ............ G01N 15/0266 324/452 |

FOREIGN PATENT DOCUMENTS

| | | | |
|---|---|---|---|
| DE | 0209755 | | 5/1908 |
| DE | 101 28 869 | A1 | 1/2002 |
| DE | 102 42 301 | A1 | 3/2004 |
| DE | 10 2009 024 782 | A1 | 2/2010 |
| DE | 102009024782 | * | 2/2010 |
| EP | 1 564 386 | A1 | 8/2005 |
| EP | 2 169 381 | A2 | 3/2010 |
| JP | 59-230153 | A | 12/1984 |
| JP | 2001-33412 | A | 2/2001 |
| JP | 2005-512042 | A | 4/2005 |
| JP | 2006-136857 | A | 6/2006 |
| JP | 2007-524786 | A | 8/2007 |
| JP | 2008-502892 | A | 1/2008 |
| JP | 2009-85959 | A | 4/2009 |
| JP | 2010-14614 | A | 1/2010 |
| JP | 5141777 | B2 | 2/2013 |
| WO | 2004/097392 | A1 | 11/2004 |
| WO | 2005/093233 | A1 | 10/2005 |
| WO | 2007/023035 | A1 | 3/2007 |
| WO | 2008/096853 | A1 | 8/2008 |

* cited by examiner

METHOD AND PARTICLE SENSOR FOR DETECTING PARTICLES IN AN EXHAUST GAS STREAM

This application is a 35 U.S.C. §371 National Stage Application of PCT/EP2011/055976, filed on Apr. 15, 2011, which claims the benefit of priority to Serial No. DE 10 2010 029 575.2, filed on Jun. 1, 2010 in Germany, the disclosures of which are incorporated herein by reference in their entirety.

BACKGROUND

The present disclosure relates to a method for detecting particles in an exhaust gas stream of a vehicle, which exhaust gas stream is guided along a duct, and to a corresponding particle sensor.

Sooty particle filters have been used for some time in order to reduce the particle emission of a diesel engine. Sensors that detect the particles in the exhaust gas can be used in order to monitor that these filters are functioning correctly or in order to be able to selectively perform the necessary regeneration phases.

WO 2004/097392 A1 discloses a sensor for detecting particles, in particular sooty particles, in a gas stream. Two measuring electrodes that are covered by a protective layer for protection purposes measure a soot concentration on the sensor surface by means of determining an electrical resistance between the measuring electrodes.

SUMMARY

On the basis of this background, a method is proposed with the present disclosure for detecting particles in an exhaust gas stream of a vehicle, which exhaust gas stream is guided along a duct, and also proposed is a particle sensor in accordance with the description below. Advantageous embodiments are disclosed in the description hereinunder.

The disclosure is based on the knowledge that it is possible to measure a dielectric constant of the exhaust gas, which dielectric constant changes as a result of the particles. Thus, for example, the dielectric constant of air $\varepsilon_{r,Air}$ is 1.0 and the dielectric constant of soot $\varepsilon_{r,Soot}$ is 19. The dielectric constant $\varepsilon_r$ can, for example, relate to a capacitance of two electrodes between which the gas that is to be measured is located. For a plate capacitor having a surface area A and a distance d between the plates, C: $C=\varepsilon_r\varepsilon_0 A/d$ applies for the capacitance.

A further core of the disclosure resides in the fact that a frequency-dependent capacitance is to be used in order to determine further properties of the particles. Thus, for example, it is possible to derive particle sizes and/or a particle size distribution from an impedance measurement. Consequently, it is possible, for example, to detect the generation of any very small particles that are medically particularly relevant.

In the case of the measuring principle in accordance with the disclosure for detecting sooty particles, it is not necessary to expose the measuring electrodes directly to the gas. Consequently, the durability and accuracy of the electrodes can be considerably increased. In addition, it is possible in an advantageous manner to derive further particle ensemble properties from the measurement of the frequency dependency of the capacitance. For example, it is possible to derive a size distribution that is not accessible with the measurement of a size.

In accordance with the approach in accordance with the disclosure, it is possible to forego the use of discharging principles in which the (ionized) sooty particles lead to a more rapid penetration of a high electrical field or to forego the use of resistive sensors that detect an electric conductivity of sooty particles that are deposited on the sensor. The discharging principles require high electrical voltages that have to be generated in the vehicle in a costly manner and are difficult to handle from the technical safety aspect. In the case of the resistive principles, it is necessary for the electrodes to be in direct contact with the exhaust gas, which can greatly impair a serviceable life of the contacts, for example as a result of corrosion, loss of adhesion etc. These disadvantages can be avoided in accordance with the disclosure.

The present disclosure provides a method for detecting particles, in particular in an exhaust gas stream of a vehicle, which exhaust gas stream is guided along a duct, using a particle sensor that comprises at least two electrodes that are arranged in the duct, wherein the method comprises the following steps: apply a first voltage and a second voltage to the at least two electrodes in order to produce a first electric field and a second electric field between the at least two electrodes; determine a first capacitance value that corresponds to the first electrical field and a second capacitance value that corresponds to the second electrical field of a capacitor that is embodied by the at least two electrodes; and ascertain from the first capacitance value and the second capacitance value information regarding the particles contained in the exhaust gas stream.

The duct can be, for example, a pipe with cut-outs in which the electrodes of the particle sensor can be arranged. The exhaust gas stream can, for example be guided along a main surface of the duct in such a manner, that said exhaust gas stream flows past the electrodes that are arranged in the duct. The particles can be, for example, sooty particles that occur together with further residual substances during the combustion of fuel in a motor vehicle and are discharged through the exhaust gas pipe of the vehicle. Sooty particles of this type can, for example, occur during the combustion of diesel fuel. The exhaust gas stream can contain a variable mass of particles and the particles can vary in size. The mass, size and also composition of the particles can vary depending upon the running time and load situation of the combustion engine. Thus, a characteristic of the particles shortly after a start-up of the combustion engine will be different to a characteristic of the particles after a longer trip. The characteristic of the particles can be determined by means of the method in accordance with the disclosure using the particle sensor at regular time intervals or in response to specific events. Generally, a plurality of determinations is performed during one trip. The particle sensor can be a capacitance sensor in which one of the at least two electrodes is used as an anode and a further of the at least two electrodes is used as a cathode. The exhaust gas stream can be guided in such a manner that at least a portion of the exhaust gas stream flows through the electric field that is produced between the electrodes. In this manner, the exhaust gas stream represents at least a portion of a dielectric between the electrodes. A dielectric constant of the dielectric is consequently dependent upon the exhaust gas stream and in particular upon a quantity and/or size of the particles of the exhaust gas stream. The dielectric constant can change in the case of a change of the composition of the exhaust gas stream. A capacitance that can be measured between the electrodes is dependent upon the dielectric constant and consequently upon the composition of the exhaust gas stream. Consequently, it is possible to determine the composition of the exhaust gas stream with the knowledge of the value of a voltage that is applied at the electrodes and a capacitance value measured between the electrodes. The first voltage and the second voltage can be applied to the electrodes sequentially, for example in an alternating manner. The voltages can have a different value and frequency. The voltage values and the frequency values can be set depending upon the type of the exhaust gas stream to be analyzed and upon the geometric shape and arrangement of the electrodes and of the duct. If the method is used in a vehicle, then, advantageously, the voltages and the frequencies have values that can be made available in the vehicle without a high expenditure. Accordingly, the first and second voltage can comprise voltage values from a voltage range of 1V to 1 kV and frequency values between direct current voltage DC and 100 MHz. These values are, however, only selected by way of example and both lower and higher values are possible. A voltage difference between the first voltage and the second voltage can be in a range of one or several volts, for example 2V, 5V, 10V, 25V, 50V or 100V, in a range of several hundred volts, for example 200V, 300V, 500V or also in the kilo volt range. A frequency difference between the first voltage and the second voltage can be in a range of several Hertz, for example 10 Hz, 25 Hz, 50 Hz or 100 Hz, in a range of several hundred Hertz, for example 200 Hz, 300 Hz, 500 Hz, in a range of several kilo Hertz, for example 200 KHz, 300 KHz, 500 KHz or in a range of one or several mega Hertz. According to an application of one of the voltages, it is possible to determine in each case an allocated capacitance value. The capacitance value can be determined by means of known measuring methods. By virtue of the fact that at least two different voltages are used, the exhaust gas stream can be exposed to at least two different electric fields that can in each case produce different dielectric constants and consequently different capacitance values. In this manner, the characteristic of the particles can be determined in a considerably more precise manner than if only a measurement has been performed with one voltage. The characteristic of the particles can be determined by comparing the capacitance values with reference values or by comparing the capacitance values with each other. It is also possible to apply one or a plurality of further voltages in order to determine one or a plurality of further capacitance values.

In accordance with one embodiment, the method can comprise a step of comparing the first capacitance value with a first reference value and of comparing the second capacitance value with a second reference value. On the basis of the comparisons it is possible to ascertain information regarding the particles contained in the exhaust gas stream. The step of comparing said values can, for example, be performed in an evaluating device in which the first and second reference value are stored. The first and second reference value can, for example, be determined in advance in the laboratory for specific vehicle and/or engine types. The reference values can represent capacitance values that correspond in each case to a specific characteristic of the particles contained in the exhaust gas stream. In dependence upon whether a capacitance value is greater, smaller or equal to a corresponding reference value, it is possible to correspondingly deduce the characteristic of the particles. The characteristic of the particles can be determined in a rapid and simple manner by comparing the capacitance values with the reference values. A suitable algorithm can be used to perform the comparison.

By way of example, if in the step of applying a voltage a direct current voltage is applied as a first voltage, it is possible in the step of comparing the first capacitance value with a first reference value to ascertain information regarding a quantity of the particles contained in the exhaust gas stream. In addition, if in the step of applying a voltage an alternating current voltage is applied as a second voltage, it is possible in the step of comparing the second capacitance value with the second reference value to ascertain information regarding a type or size of the particles contained in the exhaust gas stream. Accordingly, it is possible in the step of applying a voltage to apply a direct current voltage as a first voltage and to apply an alternating current voltage as a second voltage. Alternatively, it is also possible to apply initially an alternating current voltage and subsequently to apply a direct current voltage. Thus, it is advantageously possible to examine different properties of the particles in the exhaust gas stream in a simple and rapid manner with the aid of one and the same measuring arrangement.

Alternatively, it is possible in the step of applying a voltage to apply as a first voltage an alternating current voltage having a first frequency. An alternating current voltage having a second frequency can be applied as a second voltage. The capacitance values derived therefrom render it possible in turn to deduce the characteristic of the particles.

The different frequencies used have an effect in as much as polarized particles of a different size and/or mass orientate themselves and/or separate at different rates in the first or second electric field. Thus, for example, in the case of high frequencies only small and/or light particles can orientate themselves and/or separate in the electric field and consequently be visible as dielectric, whereas the large, non-movable particles can only contribute to the change of the effective epsilon, i.e. the dielectric constant, in the case of comparatively lower frequencies. Consequently, the frequency-dependent measurement renders it possible to determine a size distribution of the measured particles.

The present disclosure further provides a particle sensor for detecting particles in an exhaust gas stream of a vehicle, which exhaust gas stream is guided along a duct, wherein the particle sensor comprises the following features: at least two electrodes that are arranged in the duct; a device for applying a first voltage and a second voltage to the at least two electrodes in order to produce a first electric field and a second electric field between the at least two electrodes; a device for determining a first capacitance value that corresponds to the first electric field and a second capacitance value that corresponds to the second electric field of a capacitor that is embodied by the at least two electrodes; and a device for ascertaining from the first capacitance value and the second capacitance value information regarding the particles that are contained in the exhaust gas stream.

The device for applying the first and second voltage can be a voltage generator. The device for determining the first and second capacitance value can, for example, be a conventional capacitance measuring device. The capacitor can be, for example, a plate capacitor, wherein the plates that are used as electrodes can be arranged both mutually opposite and also mutually adjacent.

In accordance with one embodiment, the at least two electrodes can be arranged mutually adjacent in a flow direction of the exhaust gas stream. Consequently, a particularly space-saving arrangement of the electrodes is achieved. The particle sensor can as a result be produced with comparatively smaller dimensions and comparatively less weight.

In accordance with a further embodiment, the duct can be connected upstream and/or downstream of a particle filter. Consequently, when the duct is arranged upstream of the particle filter it is possible to monitor a combustion characteristic of the engine and when the duct is arranged downstream of the particle filter it is possible to monitor a filtering performance of the particle filter.

In addition, the duct can be embodied in order to shield the at least two electrodes from the exhaust gas stream. For example, a protective layer made from a suitable material can be applied to the cut-outs in which the electrodes are arranged. Alternatively, the electrodes can also be encased by a one-piece duct, for example, as a result of a casting method. This embodiment provides the advantage that the electrodes are not directly exposed to the exhaust gas stream. Corrosion and wear as a result of substances contained in the exhaust gas stream can be avoided and a serviceable life of the electrodes can be correspondingly extended. In addition, there is consequently no falsification of the measurement results as a result of a reaction of the electrode material with the substances in the exhaust gas stream. In addition, the duct can be embodied from an exhaust gas-resistant material. Consequently, any inadvertent exposing the electrodes as a result of a chemical reaction of the duct material with the exhaust gas stream can be avoided.

BRIEF DESCRIPTION OF THE DRAWINGS

The disclosure is explained by way of example in detail hereinunder with reference to the attached drawings, in which.

DETAILED DESCRIPTION

Figure 1:
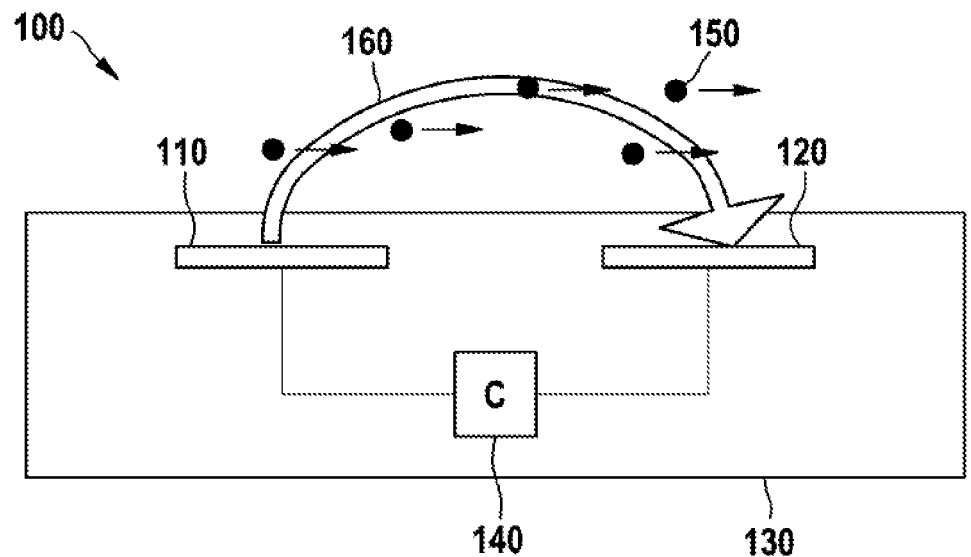
FIG. 1 shows a schematic illustration of a particle sensor in accordance with an exemplary embodiment of the present disclosure.

In the following description of preferred exemplary embodiments of the present disclosure elements that are represented in the different figures and function in a similar manner are designated by like or similar reference numerals, wherein a repeated description of these elements is omitted.

A particle sensor in accordance with the approach illustrated in this case is embodied in order to measure a number or mass of sooty particles in a gas flow. For example, sensors of this type can be installed in diesel motor vehicles downstream of a particle filter in order to check that the filter is functioning correctly or upstream of a corresponding filter in order to detect combustion properties and engine states. In general, combustion processes can be monitored using a particle filter.

FIG. 1 illustrates a schematic illustration of a particle sensor 100 in accordance with an exemplary embodiment of the present disclosure. The figure illustrates a first electrode 110, a second electrode 120, a duct 130 and a device 140 for determining a capacitance value. The duct 130 can represent a section of an exhaust gas pipe of a vehicle.

In accordance with the illustration in FIG. 1, the first electrode 110 and the second electrode 120 are at a mutually spaced disposition and are arranged at the same height in the duct 130 so that in each case a main surface of the first electrode 110 and of the second electrode 120 extend in parallel with an upper surface of the duct 130. The device 140 is connected to the electrodes 110, 120 by way of electric lines.

In accordance with the exemplary embodiment of the particle sensor 100 illustrated in the figure, the electrodes 110, 120 are fully encased by the material of the duct 130. An exhaust gas stream that comprises a plurality of particles 150 flows in a direction that is indicated by a plurality of arrows along the upper surface of the duct 130. For the sake of clarity, only one of the particles 150 is provided with a reference numeral. A direction of an electrical field 160 between the electrodes 110, 120 is indicated in the exemplary embodiment of the particle sensor 100 illustrated in FIG. 1 by an arrow from the first electrode 110 to the second electrode 120. The electric field 160 is produced by the electrodes 110, 120 if the electrodes 110, 120 comprise different electrical potentials. The different electric potentials can be produced in that a voltage is applied between the two electrodes 110, 120 by way of the device 140. The electric field 160 can also extend in the opposite direction or the direction can change continuously depending upon whether a direct current voltage or an alternating current voltage is applied to the electrodes 110, 120. The device 140 is embodied in order to apply different voltages sequentially to the electrodes 110, 120. In this case, the device 140 can provide two or more different voltages for applying to the electrodes 110, 120. The different voltages can be applied to the electrodes 110, 120 within a time frame that is dimensioned so short that the characteristic of the particles 150 in the exhaust gas stream typically do not change within the time frame.

In addition, the device 140 is embodied in order to measure at the electrodes 110, 120 the capacitance values that result from the different voltages. It is possible to determine the characteristic, for example the number and type, of the particles 150 by means of suitably evaluating the capacitance values in the device 140 or in a separate evaluating device.

The illustration in FIG. 1 illustrates a measurement of a change in the capacitance of the two electrodes and/or capacitor plates 110, 120 by means of the dielectric constant of the sooty particles 150. The electrodes 110, 120 can in this case be protected by an exhaust gas-resistant material of the duct 130. Consequently, the measuring electrodes 110, 120 are not exposed to the gas to be measured, which results in a longer serviceable life of the electrodes 110, 120.

In accordance with the exemplary embodiment of the disclosure illustrated in FIG. 1, the gas containing the particles 150 that are to be measured enters the electric field 160 that is embodied between the two electrodes 110, 120 that are arranged as desired and to which a voltage is applied. For example, the electrodes 110, 120 can be embodied as opened-up plates of a plate capacitor, as a result of which the production can be considerably simplified since the functional elements are located in one plane. In dependence upon a number of sooty particles 150, the effective dielectric constant between the two electrodes 110, 120 changes, which can be determined by way of measuring the capacitance. If the capacitance measurement is performed at different frequencies, i.e. if an alternating current voltage is applied to the electrodes 110, 120, only specific particles 150 participate in a dielectric change since the particles 150 can orientate themselves at different rates in the electric field 160 depending upon size and type. As a consequence, it is not only possible to determine the number of particles 150 from an alternating current voltage capacitance measurement or impedance measurement but it is also possible to determine a composition of an ensemble of particles 150.

Figure 2:
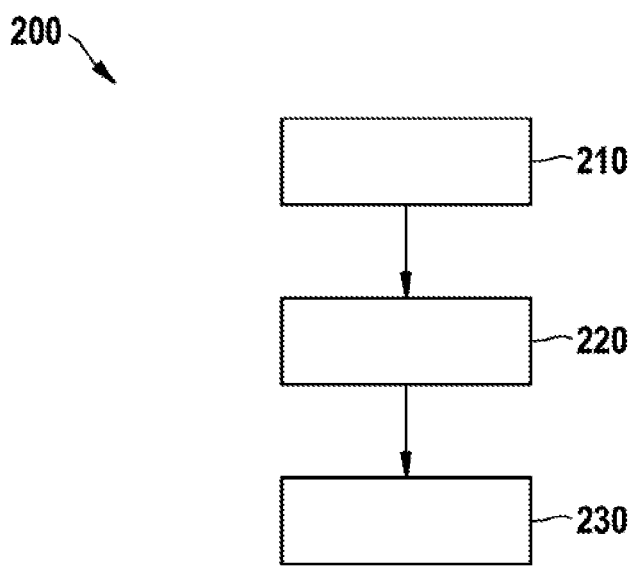
FIG. 2 shows a flow chart of a method for detecting particles in an exhaust gas stream in accordance with an exemplary embodiment of the present disclosure.

FIG. 2 illustrates a flow chart of a method 200 in accordance with an exemplary embodiment of the present disclosure. In accordance with the method 200, particles in an exhaust gas stream that is guided in a duct can be detected by means of a particle sensor, for example by means of the particle sensor illustrated in FIG. 1. In a step 210, different voltages are applied sequentially to the at least two electrodes of the particle sensor. For example, it is possible to apply initially a direct current voltage and subsequently to apply an alternating current voltage to the electrodes. Alternatively, it is also possible to apply to the electrodes successively alternating current voltages having different frequencies or to apply initially an alternating current voltage and then a direct current voltage. An electric field builds up between the electrodes according to the type and/or frequency of the applied voltage, through which electric field flows the exhaust gas stream that is guided along the duct of the particle sensor. With the application of the voltage, the at least two electrodes form an electrically charged capacitor. Depending upon a dielectric constant of the exhaust gas, which dielectric constant changes as a result of the type and/or quantity of the particles in the exhaust gas stream, the electric field that is produced by means of the applied voltage between the at least two electrodes changes. In a step 220, a capacitance value of the capacitor that is formed by the electrodes is determined, which capacitance value corresponds to the prevailing electric field. Consequently, a capacitance value is determined in the step 220 for each voltage that is applied in the step 210. In a step 230, information regarding the particles contained in the exhaust gas stream is ascertained from the capacitance values determined in the step 220 and said information is provided for further processing.

The steps 210, 220, 230 of the method 200 can be repeated as often as desired during a vehicle trip, so that precise information regarding the content and/or the type of particles in the exhaust gas stream of the vehicle can be constantly obtained. It is also possible initially, for example based on two different capacitance values, to ascertain initial information regarding the particles contained in the exhaust gas stream, and based on the initial information further voltages that match the initial information can be applied to the electrodes in order to determine further capacitance values based on which detailed information regarding the particles contained in the exhaust gas stream can be ascertained.

The exemplary embodiments described and illustrated in the figures are selected only by way of example. Different exemplary embodiments can be combined with each other fully or with regard to individual features. An exemplary embodiment can also be supplemented by features of a further exemplary embodiment. If an exemplary embodiment comprises an "and/or" link between a first feature and a second feature, then this can be read in such a manner that the exemplary embodiment in accordance with one embodiment comprises both the first feature and also the second feature and in accordance with a further embodiment comprises either only the first feature or only the second feature.

The particle sensor presented here on the basis of a capacitance measurement and/or an impedance measurement can be used, for example, in the vehicle, for example as an on-board diagnosis sensor for the particle filter. It is also feasible that it can be used as a general sensor for monitoring combustion processes, for example in fire detectors, heating installations etc.

The invention claimed is:

1. A method for detecting particles in an exhaust gas stream guided along a duct using a particle sensor that comprises at least two electrodes arranged in the duct, the method comprising:
    applying a first voltage and a second voltage to the at least two electrodes to produce a first electric field and a second electric field between the at least two electrodes;
    determining a first capacitance value that corresponds to the first electrical field and a second capacitance value that corresponds to the second electrical field of a capacitor that is embodied by the at least two electrodes;
    ascertaining from the first capacitance value and the second capacitance value information regarding the particles contained in the exhaust gas stream; and
    comparing the first capacitance value with a first reference value and comparing the second capacitance value with a second reference value to ascertain information regarding the particles contained in the exhaust gas stream,
    wherein the second capacitance value is compared with the second reference value to ascertain information regarding a type or size of the particles contained in the exhaust gas stream when the second voltage is an alternating current voltage.

2. The method as claimed in claim 1, wherein the first capacitance value is compared with a first reference value to ascertain information regarding a quantity of the particles contained in the exhaust gas stream when the first voltage is a direct current voltage.

3. The method as claimed in claim 1, wherein the first voltage is a direct current voltage and the second voltage is an alternating current voltage.

4. The method as claimed in claim 1, wherein the first voltage is an alternating current voltage having a first frequency and the second voltage is an alternating current having a second frequency.

5. A particle sensor for detecting particles in an exhaust gas stream guided along a duct of a vehicle comprising:
    at least two electrodes arranged in the duct;
    a device configured to apply a first voltage and a second voltage to the at least two electrodes to produce a first electric field and a second electric field between the at least two electrodes;
    a device configured to determine a first capacitance value that corresponds to the first electric field and a second capacitance value that corresponds to the second electric field of a capacitor that is embodied by the at least two electrodes;
    a device configured to compare the first capacitance value with a first reference value and comparing the second capacitance value with a second reference value to ascertain information regarding the particles contained in the exhaust gas stream,
    wherein the second capacitance value is compared with the second reference value to ascertain information regarding a type or size of the particles contained in the exhaust gas stream when the second voltage is an alternating current voltage.

6. The particle sensor as claimed in claim 5, wherein the at least two electrodes are arranged mutually adjacent in a flow direction of the exhaust gas stream.

7. The particle sensor as claimed in claim 5, wherein the duct is configured to protect the at least two electrodes from the exhaust gas stream.

8. The particle sensor as claimed in claim 5, wherein the duct is formed from an exhaust gas-resistant material.

9. A method for detecting particles in an exhaust gas stream guided along a duct using a particle sensor that comprises at least two electrodes arranged in the duct, the method comprising:
    applying a first voltage and a second voltage to the at least two electrodes to produce a first electric field and a second electric field between the at least two electrodes;
    determining a first capacitance value that corresponds to the first electrical field and a second capacitance value that corresponds to the second electrical field of a capacitor that is embodied by the at least two electrodes;
    ascertaining from the first capacitance value and the second capacitance value information regarding the particles contained in the exhaust gas stream; and
    comparing the first capacitance value with a first reference value and comparing the second capacitance value with a second reference value to ascertain information regarding the particles contained in the exhaust gas stream,
wherein the first voltage is a direct current voltage and the second voltage is an alternating current voltage.

* * * * *